(12) United States Patent
Bongiorno et al.

(10) Patent No.: US 11,439,370 B2
(45) Date of Patent: Sep. 13, 2022

(54) SYSTEM AND APPARATUS FOR FERTILITY AND HORMONAL CYCLE AWARENESS

(71) Applicant: Humane, Inc., San Francisco, CA (US)

(72) Inventors: Bethany Bongiorno, San Francisco, CA (US); Imran A. Chaudhri, San Francisco, CA (US)

(73) Assignee: Humane, Inc., San Francisco, CA (US)

( * ) Notice: Subject to any disclaimer, the term of this patent is extended or adjusted under 35 U.S.C. 154(b) by 0 days.

(21) Appl. No.: 15/976,614

(22) Filed: May 10, 2018

(65) Prior Publication Data
US 2018/0325498 A1   Nov. 15, 2018

Related U.S. Application Data

(60) Provisional application No. 62/504,495, filed on May 10, 2017.

(51) Int. Cl.
*A61B 5/01* (2006.01)
*A61B 10/00* (2006.01)
(Continued)

(52) U.S. Cl.
CPC ............ *A61B 10/0012* (2013.01); *A61B 5/01* (2013.01); *A61B 5/7267* (2013.01); *A61B 5/7282* (2013.01); *A61B 5/742* (2013.01); *A61B 5/749* (2013.01); *A61B 5/7475* (2013.01); *A61B 5/14517* (2013.01); *A61B 5/14546* (2013.01); *A61B 5/4266* (2013.01); *A61B 2010/0019* (2013.01); *A61B 2560/0214* (2013.01); *A61B 2560/0456* (2013.01); *A61B 2560/0493* (2013.01); *A61B 2562/0271* (2013.01); *A61B 2562/08* (2013.01)

(58) Field of Classification Search
CPC ....... A61B 5/01; A61B 5/7267; A61B 5/7282; A61B 5/742; A61B 5/7475; A61B 5/749; A61B 5/14517; A61B 5/14546; A61B 5/4266; A61B 10/0012; A61B 2010/0019; A61B 2560/0214; A61B 2560/0456; A61B 2560/0493; A61B 2562/0271; A61B 2562/08
See application file for complete search history.

(56) References Cited

U.S. PATENT DOCUMENTS

| 4,151,831 A | 5/1979 | Lester |
| 4,465,077 A | 8/1984 | Schneider |

(Continued)

FOREIGN PATENT DOCUMENTS

| GB | 2533615 | 6/2016 |
| JP | 2011522246 A | 7/2011 |

(Continued)

OTHER PUBLICATIONS

PCT International Preliminary Report on Patentability in International Appln. No. PCT/US2018/032069, dated Nov. 21, 2019, 12 pages.

(Continued)

*Primary Examiner* — Ankit D Tejani
*Assistant Examiner* — Joshua Brendon Solomon
(74) *Attorney, Agent, or Firm* — Fish & Richardson P.C.

(57) ABSTRACT

A system and apparatus is disclosed for indicating a window of fertility based on the fertility awareness method (FAM).

17 Claims, 3 Drawing Sheets

(51) Int. Cl.
*A61B 5/00* (2006.01)
*A61B 5/145* (2006.01)

(56) References Cited

U.S. PATENT DOCUMENTS

| | | | |
|---|---|---|---|
| 4,559,598 A | 12/1985 | Goldwasser et al. | |
| 4,704,696 A | 11/1987 | Reimer et al. | |
| 7,284,428 B1 | 10/2007 | Hoben et al. | |
| 7,966,647 B1 | 6/2011 | Goe | |
| 8,868,927 B1 | 10/2014 | Lee et al. | |
| 2004/0039254 A1 | 2/2004 | Stivoric et al. | |
| 2004/0081024 A1 | 4/2004 | Weng | |
| 2004/0100376 A1 | 5/2004 | Lye et al. | |
| 2005/0027208 A1* | 2/2005 | Shiraishi | E03D 9/08 600/551 |
| 2008/0001577 A1 | 1/2008 | Sather et al. | |
| 2009/0234200 A1 | 9/2009 | Husheer | |
| 2010/0109946 A1* | 5/2010 | Pande | A01B 79/005 707/759 |
| 2010/0312137 A1* | 12/2010 | Gilmour | G01N 33/558 600/551 |
| 2012/0158098 A1* | 6/2012 | Wesselink | A61B 5/107 607/62 |
| 2016/0066894 A1* | 3/2016 | Barton-Sweeney | A61B 5/0836 600/301 |
| 2016/0139156 A1 | 5/2016 | Lakdawala | |
| 2016/0287148 A1 | 10/2016 | Coresyte | |
| 2016/0327553 A1 | 11/2016 | Edwards et al. | |
| 2016/0331244 A1* | 11/2016 | Barton-Sweeney | A61B 5/024 |
| 2017/0258455 A1* | 9/2017 | Qi | A61B 10/0012 |
| 2018/0153451 A1* | 6/2018 | Heikenfeld | A61B 5/01 |
| 2018/0206729 A1* | 7/2018 | Wang | A61B 5/01 |
| 2018/0214028 A1* | 8/2018 | Zhang | A61B 5/4318 |
| 2019/0167236 A1* | 6/2019 | Maas | A61B 10/0012 |

FOREIGN PATENT DOCUMENTS

| | | |
|---|---|---|
| JP | 2012070920 A | 4/2012 |
| JP | 2014504517 A | 2/2014 |
| JP | 2016153978 A | 8/2016 |
| TW | 563517 U | 11/2003 |
| WO | WO 2015/143259 | 9/2015 |
| WO | WO 2015179015 | 11/2015 |
| WO | WO 2016069052 | 5/2016 |
| WO | WO 2017015661 | 1/2017 |

OTHER PUBLICATIONS

PCT International Search Report and Written Opinion in International Application No. PCT/US2018/032069, dated Aug. 24, 2018, 15 pages.

EP Supplementary European Search Report and Written Opinion in European Appln. No. 18797781.4, dated Apr. 29, 2021, 14 pages.

EP Supplementary Partial European Search Report and Written Opinion in European Appln. No. 18797781.4, dated Jan. 19, 2021, 13 pages.

* cited by examiner

SYSTEM AND APPARATUS FOR FERTILITY AND HORMONAL CYCLE AWARENESS

CROSS-RELATED APPLICATION

This application claims the benefit of priority from U.S. Provisional Patent Application No. 62/504,495, for "Device for Indicating Window of Fertility Based on Basal Body Temperature and User Profile," filed May 10, 2017, which patent application is incorporated by reference herein in its entirety.

TECHNICAL FIELD

This disclosure relates generally to fertility monitoring and hormonal cycle awareness.

BACKGROUND

A woman's fertile window is the day that she ovulates and the five days, leading up to that day. The last day of her fertile window, called ovulation, is the phase of her cycle when one of her ovaries releases an egg into her fallopian tube, where it awaits her partner's sperm for fertilization. Once released, an egg only has a lifespan of about 24 hours to be fertilized. If the egg is not fertilized, it disintegrates, triggering her next period. Even though the egg is only viable for 24 hours, her partner's sperm are able to survive and fertilize the egg for up to five days after intercourse, so any intercourse within five days of ovulation could result in conception. The closer the intercourse is to ovulation the higher the likelihood of conception.

Conventional wisdom is that ovulation occurs about halfway through a cycle, or 14 days after the female starts her period. The time of ovulation can differ greatly from woman to woman and even cycle to cycle, depending on the length and consistency of a woman's cycle and any outside influences (e.g., stress, malnutrition). In the past, people have relied on a number of different methods to predict ovulation. Some methods rely on data logging of fertility data including basal body temperature, cervical fluid, physical symptoms, etc. Basal body temperature (BBT) is the lowest body temperature attained during rest (e.g., during sleep). BBT is can be estimated by a temperature measurement immediately after awakening and before any physical activity has been undertaken. This measurement will lead to a somewhat higher value than the true BBT.

In most women, ovulation causes a sustained increase of at least 0.2° C. (0.4° F.) in BBT. Monitoring BBTs is one way of estimating the day of ovulation. The tendency of a woman to have lower temperatures before ovulation, and higher temperatures afterwards, is known as a biphasic temperature pattern. Charting this pattern may be used as a component of fertility awareness.

One worldwide problem with fertility awareness is the lack of education and accessibility. Natural birth control/fertility control methods are not easily accessible. Natural birth control/fertility control methods are not taught, encouraged or made accessible by educators, doctors, pharmaceutical companies, etc. Those seeking to get pregnant are often pushed into invasive methods when they are having trouble conceiving, rather than being given the proper education and insight to give themselves the best possible chance of conceiving, as well as identifying what the underlying problems may be. Those seeking not to get pregnant are often pushed into invasive methods, rather than being given the appropriate information about all available options. In sum, couples have lost touch with the natural way their bodies work and work together. They communicate more with pharmaceutical companies and doctors than with their own bodies or with each other.

Existing natural birth control/fertility control methods are complex, confusing and clumsy. Existing birth control methods, such as birth control pills, condoms and the intrauterine contraceptive device (IUD) are invasive. These methods have numerous and serious immediate side effects, such as increased risk of stroke, weight gain, cramping, infertility, decreased sex drive, pelvic inflammatory disease (PID), uterine perforation, etc. There are also long term side effects such as increased rate of cervical cancer. Birth control methods are also expensive and can have a negative impact on relationships. For example, most birth control methods fall heavily on the woman. As a result, relationships can suffer because of the difficulty in communication when it comes to issues surrounding birth control and fertility. A lack of insight can lead to a breakdown in communication between couples.

SUMMARY

A system and apparatus is disclosed for indicating a window of fertility based on the fertility awareness method (FAM).

In an embodiment, an apparatus comprises: a housing having a top surface and a bottom surface; a temperature sensor disposed on the bottom surface; a charge circuit and one or more charge electrodes or contacts configured to charge the apparatus when the apparatus is docked in a charging dock; an output port configured to transfer data to the docking station when the apparatus is docked; a printed circuit board disposed within the housing and including: one or more processors coupled to the temperature sensor; memory storing computer-readable instructions that when executed by the one or more processors, cause the one or more processors to perform operations comprising: obtaining, by the one or more processors, a user's basal body temperature reading from the temperature sensor; storing, by the one or more processors, the user's basal body temperature reading in the memory; determining, by the one or more processors, that the apparatus is docked in the docking station; and transferring, by the one or more processors, the basal body temperature reading from the memory to the output port.

In an embodiment, an apparatus comprises: a housing having a top surface and a bottom surface, the top surface having a recess for receiving a fertility awareness (FA) apparatus; an ambient light indicator system disposed within the housing and including one or more ambient light sources; a printed circuit board disposed within the housing and including: one or more processors coupled to the ambient light indicator system; memory storing computer-readable instructions that when executed by the one or more processors, cause the one or more processors to perform operations comprising: obtaining, by the one or more processors, one or more basal body temperature readings from an output port of the FA device and user input data from memory; determining, by the one or more processors, fertility awareness information from the basal body temperature readings and the user input data; responsive to the determining, commanding, by the one or more processors, the ambient light indicator system to activate or deactivate one or more ambient lights in accordance with the fertility awareness information to indicate a fertility status.

In an embodiment, a method comprises: obtaining, by a biosensor, basal body temperature readings of a user; determining, by a processor, a fertility status of the user based on the basal body temperature readings and user input data; selecting, by the one or more processors and based on the determined fertility status, an ambient light color; and activating, one or more ambient light sources having the selected ambient light color.

Particular embodiments disclosed herein provide one or more of the following advantages. The disclosed system and apparatus allows a use to simply take back control of their body. The system and apparatus is less expensive and more accessible than convention fertility awareness products. The apparatus can be used as a family heirloom to be passed down along with education about our bodies and how they are meant to work (e.g., minimal software updates, no dependencies on other devices). The system and apparatus can be part of a fertility awareness program where product purchases offset donations of the product to parts of the world that are most in need of birth control solutions. The fertility awareness and hormonal cycle information the system and apparatus provides can be used by a woman for her entire lifespan, from puberty to menopause.

The system and apparatus helps give couples improved chances of achieving pregnancy or avoid pregnancy. The system and apparatus helps women get back in touch with their bodies, giving them insight into what is going on inside their body and between the couple. The system and apparatus helps improve communication between a woman and her body, feel powerful, more in tune and quickly identify problems as they arise, and also improve communication with her partner. The system and apparatus can help couples improve their relationship by removing complex, messy birth control methods and removes hormonal birth control difficulties (e.g., reduced sex drive, hormonal fluctuations, etc.)

The details of the disclosed embodiments are set forth in the accompanying drawings and the description below. Other features, objects and advantages are apparent from the description, drawings and claims.

DESCRIPTION OF DRAWINGS

The same reference symbol used in various drawings indicates like elements.

DETAILED DESCRIPTION

Overview

FAM is a way to predict fertile and infertile times in a woman's cycle. FAM is based on body signs, which change during each menstrual cycle in response to the hormones that cause ovulation. If trying not to get pregnant, when followed correctly, the FAM can reach over 99% effectiveness in preventing pregnancy. If trying to get pregnant, following the FAM dramatically increases the probability of conceiving. To assist a couple is practicing FAM, a light weight, small form factor fertility awareness system (FAS) is disclosed.

The FAS stores data securely without a companion application or device. The FAS is user navigated with a simple user interface (UI). In an embodiment, the FAS includes a bed side charging dock with an ambient indicator light system. FAS includes wired and wireless connectivity and/or one or more output ports (e.g., universal serial bus (USB), Thunderbolt®) to allow the user to easily and securely share data with their doctor. The FAMD can include a rechargeable battery that can be recharged from photovoltaic cells to allow for on-the-go charging. In an embodiment, the FAS includes circuitry for inductive charging of the rechargeable battery using a charge mat. In another embodiment, the FAS includes circuitry for over-the-air (OTA) wireless charging.

The FAS is configured to store FAM information that can educate a couple on how their body and bodies work together. It tracks the woman's cycle, and therefore fertile and infertile periods using input data (multiple data points) and BBT. In an embodiment, software running on the device uses machine learning technology to learn the woman's cycle and pushes and pulls data based on where the woman is in her cycle. The FAS automatically and naturally (in an ambient manner via the charging dock indicator light system) lets the couple know when the woman is fertile or not fertile, and when the woman is most fertile, and there when the couple should or should not have sex without a barrier method based on whether the couple is trying to get pregnant or prevent pregnancy.

In addition to detecting and diagnosing potential issues or barriers to pregnancy, the data collected by the FAS can be securely shared with a doctor or other medical professional to review and discuss any anomalies. Also, the collected data allows a user to understand how her fluctuating hormone levels throughout her cycle can provide her insight into her physical, mental and emotional state and well-being. Such insight can be valuable at many points throughout the user's life cycle, such as during puberty, fertile years and menopause.

Example Fertility Awareness System

Figure 1A:
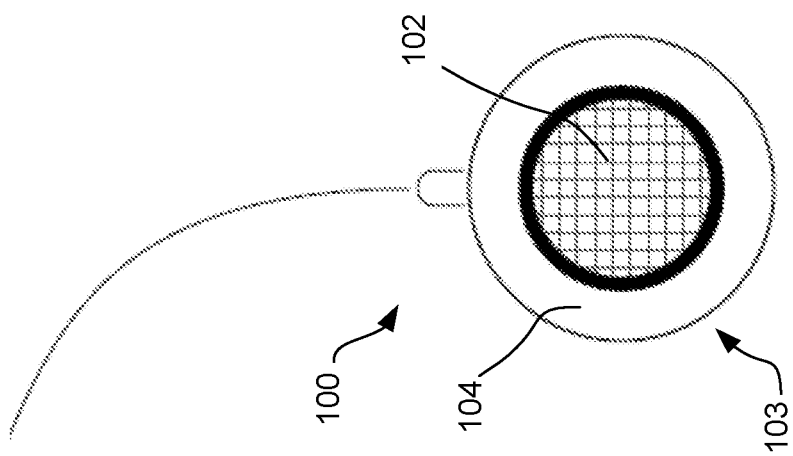
FIG. 1A is a top view of a fertility awareness system (FAS), according to an embodiment.

FIG. 1A is a top view of FAS 100, according to an embodiment. In the example shown, FAS 100 includes FA device 102 and charging dock 103. FA device 102 and/or charging dock 103 can include a touch-sensitive surface or display that responds to touch input, such as one or more taps for turning FA device 102 and/or charging dock 103 on or off, checking battery life, staring a set-up procedure, etc. In the example embodiment shown, charging dock 103 includes an electrical cord for connecting to an outlet and/or a USB port for connection and receiving power from another electronic device (e.g., a computer). Charging dock 103 can also include a rechargeable battery and charge circuits for inductive or OTA wireless charging.

FA device 102 can be placed by the user in a recessed area of charging dock 103. When placed in the recessed area, one or more charging electrodes/contacts on the bottom of FA device 102 (not shown) electrically connect with charging electrodes/contacts in the recessed area to facilitate charging of FA device 102 by charging dock 103. In the example shown, FA device 102 and charging dock 103 both have disc-shaped housing. Any desired form factor, however, can be used for FA device 102 and charging dock 103, including different shape form factors for FA device 102 and charging dock 103.

In an embodiment, FA device 102 and/or charging dock 103 can ask the user questions regarding her menstrual cycle using an audio subsystem. These questions can be asked during a set-up of FAS 100. In an embodiment, a wired or wireless keyboard, or dedicated remote device (e.g., smart phone, tablet computer) can be used to enter answers into FAS 102 and/or charging dock 103 through a wireless or wired connection. In an embodiment, the questions can be answered by the user with their desktop computer using a full size keyboard. The answers can be downloaded to FAS 100 over the user's wireless local area network (e.g., WiFi, Bluetooth) or through an over-the-air (OTA) wireless network (e.g., a cellular network). In an embodiment the questions can be asked using the synthesized voice or digital assistant. For example, during the set-up, FAS 100 can ask questions through synthesized speech through a loudspeaker on FA device 102 and/or charging station 103 (not shown) and receive the user's answers through one or more microphones (not shown) on FA device 102 and/or charging station 103. The questions can be presented in any desired format, including but not limited to: a yes/no format, check boxes, text input fields, touch input, etc.

During initialization, in some embodiment the user can enter a WiFi password to connect FAS 100 to the user's wireless local area network (e.g., WiFi network). After initialization, FAS 100 can be responsive to voice commands and provide additional services, such as connecting to the Internet, responding to user questions, reading the news, searching the Web, making online purchases, making telephone calls, ordering food or services, playing music, etc. In an embodiment, FA device 102 and/or charging dock 103 can include a touch-sensitive display that responds to touch input and also displays information, including the aforementioned questions. In an embodiment, FA device 102 and/or charging dock 103 can include a media player for playing music. In an embodiment, charging dock 103 can also be a digital alarm clock that can be programmed by the user using one or more mechanical buttons or through a wireless or wired connection by another device (e.g., a wireless keyboard).

Charging dock 103 includes ambient light indicator system (ALIS) 104 for providing visual feedback regarding fertility status to the couple using different colored lights. After processing the collected user input data and temperature readings, FAS 100 will indicate fertility status based on the couple's preference of wanting to avoid pregnancy or be aided in pregnancy. For example, when FAS 100 determines that the user is in her fertility window, the ambient light indicator system turns, for example, green or red, and when the user is not in her fertility window, the ambient light indicator system 104 turns, for example, red or green. Any color or color scheme can be used to provide visual feedback. Also, a different color can be used to signal a time of maximum fertility or a time of minimum fertility.

In an embodiment, the lights can blink in a pattern or alternate between colors in a pattern to provide feedback about the user's fertility window or other information (e.g., remaining battery power). In an embodiment, FAS 100 can provide different or additional feedback other than visual, such as audio feedback by playing certain music or other audio cues (e.g., sound effects, jingle, ringtone, synthetic speech). In an embodiment, FAS 100 sends a message or notification regarding the fertility window to another user device (e.g., smart phone, tablet computer) through the user's wireless local area network or short range communication link (Bluetooth, near field, ZigBee™) and a wide area network (e.g., the Internet).

Figure 1B:
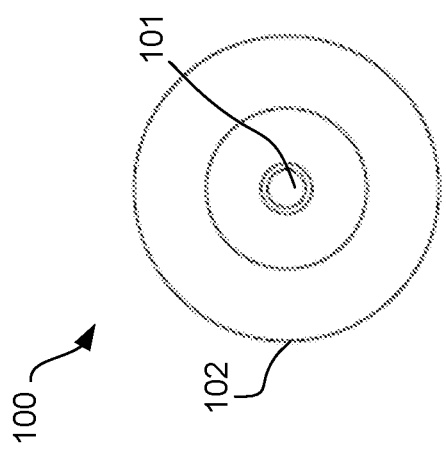
FIG. 1B is bottom view of a fertility awareness (FA) device of FIG. 1A, according to an embodiment.

FIG. 1B is bottom view of FA device 102, according to an embodiment. The bottom of FA device 102 includes temperature sensor 101. The user can place temperature sensor 101 against her forehead for a specified period of time (e.g., each morning after waking up) to measure and register her basal body temperature with FAS 100. For example, the FA device 102 can be placed in charging dock 103 which can be placed on the user's bedside table. When the user wakes in the morning, she can place temperature sensor 101 on her forehead and take her own temperature without having to leave her bed. Each morning, the user can perform a "check-in" with FAS 100 by answering questions asked by digital assistant FAS 100 after taking her temperature. This allows FAS 100 to collect data at different points or phases in the user's menstrual cycle, which can be used by FAS 100 to predict a fertility window and/or a time of maximum fertility if the user is trying to get pregnant or time of minimum fertility if the user is trying to avoid pregnancy.

In an embodiment, when FA device 102 is placed in charging dock 103, FA device 102 transfers the collected temperature readings into a memory (e.g., flash memory) in charging station 103. In an embodiment, FA device 102 and charging dock 103 are wired or wirelessly (e.g., through Bluetooth) connected to each other so that the temperature readings can be transferred wirelessly over a wireless communication link.

In an embodiment, in addition to basal body temperature readings, FAS 100 uses other hormonal biomarkers provided by different types of embedded biosensors to determine a fertility window or hormonal cycle. For example, an embedded biosensor can be used to detect chloride ion concentration changes in perspiration on the skin. In an embodiment, an external sensor can be coupled to charging dock 103 using a wired or wireless connection, such as an electronic device for detecting a change in the concentration of the female hormone human chorionic gonadotropin (hCG) and luteinizing hormone (LH) in urine. The hCG hormone is released by a fertilized ovum and the presence of this hormone in urine is a marker for indicating pregnancy.

In an embodiment, other sensors can be included in FAS 100 to track hormone changes throughout the user's cycle. Thus, FAS 100 can be used not only for getting pregnant and pregnancy avoidance, but also for puberty, menopause and overall cycle awareness. Some examples of sensors include but are not limited to transdermal sensors and a sensor for detecting estrogen levels in saliva. For example, when the user is about to ovulate, her saliva begins to form a distinct fern-like pattern when viewed under a microscope due to an increase in the level of estrogen present in her body, which causes and increase in salinity. In an embodiment, FA device 102 and/or charging dock 103 can include a personal microscope that illuminates ferning in the user's saliva. The user can use the microscope to see visual changes in her saliva throughout her cycle and predict her ovulation as much as 72 hours in advance. In an alternative embodiment, FA device 102 and/or charging dock 103 can include a port for attaching to a personal microscope accessory or a transdermal sensor.

Figure 1C:
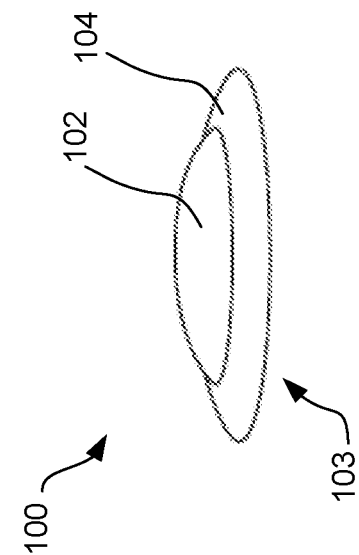
FIG. 1C is a side view of the FAS, according to an embodiment.

FIG. 1C is a side view of FAS 100 showing FA device 102, charging dock 103 and ambient light indicator system 104. Note that information collected by FAS 102 can be uploaded to a user's online account (in the cloud) and then downloaded on other FA devices. For example, if the couple has two homes, there can be a FAS 100 in each home and both will be automatically or manually updated or synced with information collected from the other FAS at the other location.

Figure 2:
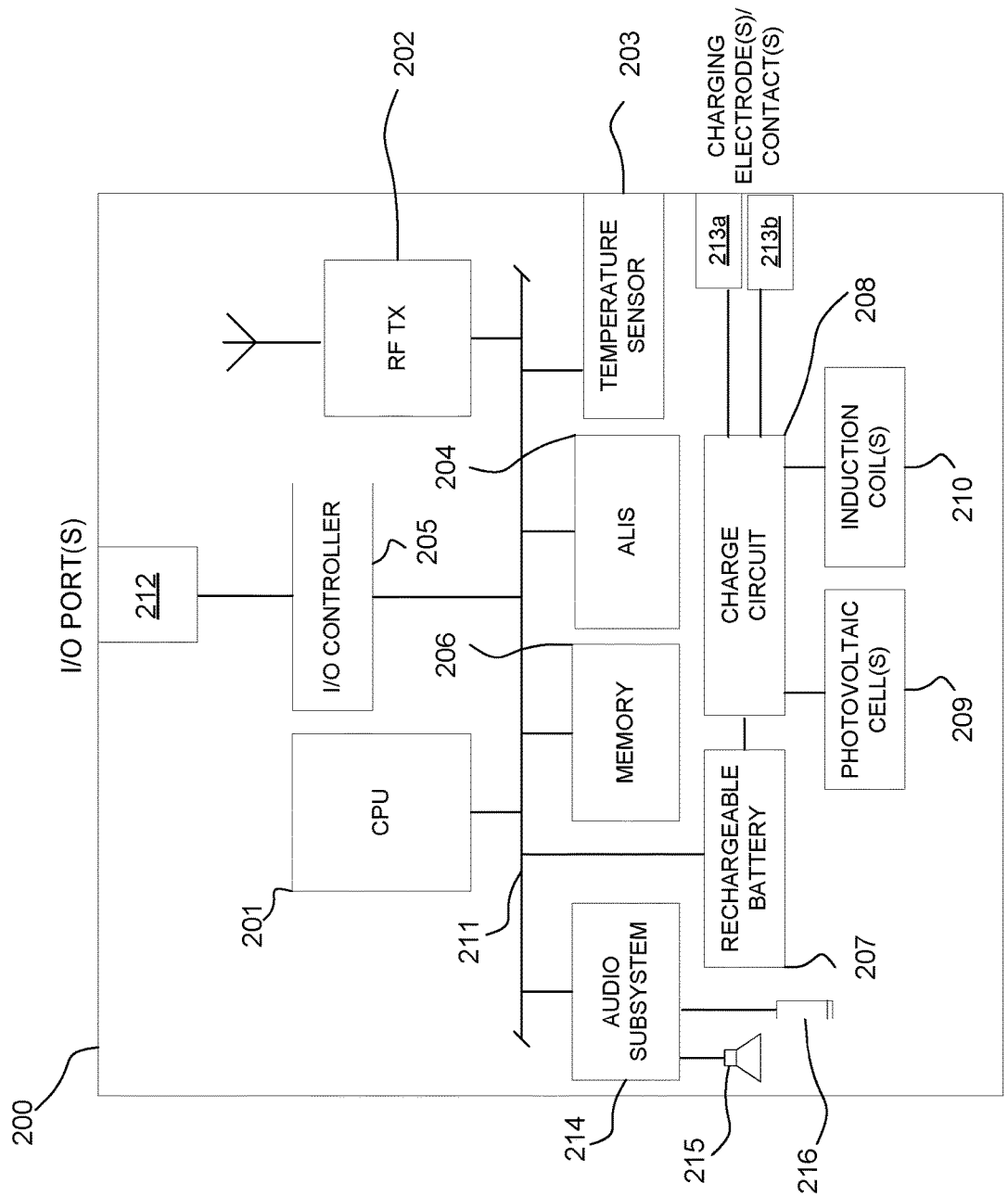
FIG. 2 is block diagram of the FA device/charging dock architecture, according to an embodiment.

FIG. 2 is block diagram of the FA device/charging dock architecture 200, according to an embodiment. Architecture 200 can be used for either FA device 102 and/or charging dock 103, except that the temperature sensor 203 and audio subsystem 214, loudspeaker 215 and microphone(s) 216 would likely be included in the FA device 102 rather than the charging dock 103. Architecture 200 can be included on a printed circuit board (PCB) within a housing of FA device 102 or charging dock 103.

In the example embodiment shown, architecture 200 includes central processing unit (CPU) 201, radio frequency (RF) transceiver 202, temperature sensor 203, ambient light indicator system (ALIS) 204, I/O controller 205, memory 206, rechargeable battery 207, charge circuit 208, photovoltaic cell(s) 209, induction coil(s) 210, bus 211, I/O port(s) 212, charge electrodes/contacts 213a, 213b, audio subsystem 214, loudspeaker 215 and microphone(s) 216.

During set-up the user is asked questions regarding her menstrual cycle and other information (e.g., age, weight, health issues). In an embodiment, the questions can be asked using spoken questions from audio subsystem 214 (e.g., from a digital assistant). The user's spoken responses are interpreted by a speech recognition system implemented by audio subsystem 214 and stored in memory 206 as user input data. In an embodiment, the user input data is encrypted in memory 206 for privacy.

The FAS 100 uses the temperature-based FAM. The user's body temperature naturally changes a small amount throughout her menstrual cycle. It is lower in the first part of her cycle, and then rises when she ovulates. For most people, 96-98 degrees Fahrenheit is their typical temperature before ovulation. After she ovulates, it goes up to 97-99° F. To use the temperature method, the user takes her temperature reading using temperature sensor 203 of FA device 102 every single day. The temperature readings are stored in memory 206 and transferred to charging dock 103 when FA device 102 is docked.

In an embodiment, CPU 201 in charging dock 103 maintains a mapping in memory of user temperature and menstrual cycle days. Using the mapping, CPU 201 determines fertility awareness information including "safe" days for vaginal intercourse. For example, safe days begin after the increase in the user's temperature lasts for at least 3 days, and end when the user's temperature drops just before her next period begins. During her safe days, the user can have unprotected vaginal intercourse. On her unsafe (fertile) days, she can avoid vaginal intercourse or use another method of birth control. Based on the determined safe days, CPU 210 commands ALIS 204 to activate or deactivate one or more ambient light sources, such as, for example, light-emitting diodes (LEDs) or active-matrix organic light-emitting diode (AMOLED). For example, if the couple wants to avoid pregnancy, ALIS 204 can activate a red ambient light on unsafe days and a green light on safe days. If the couple wants pregnancy assistance, then ALIS 204 can activate a green ambient light (e.g., green LED) at a time of maximum fertility and red light (e.g., red LED) at a time of minimum fertility. If the charging dock is on a bed side table in the couple's bedroom, or in another prominent but private location, the couple is alerted of the fertility window.

In an embodiment, a history of basal temperature readings and/or user input data (e.g., the user's age, beginning of the user's cycle, the length of the user's cycle, dates of vaginal intercourse, known fertility problems) are input to a machine learning algorithm implemented by CPU 201 to predict a fertility window or event. Any suitable machine learning or artificial intelligence algorithm can be used to make the prediction (e.g., deep learning or conventional neural networks, support vector machine, regression or clustering techniques).

Other features of architecture 200 includes wireless transceiver 202 for communicating with a wireless local area network (e.g., WiFi) or short range communication (e.g., Bluetooth, RFID). This allows the fertility awareness information to be uploaded to the cloud and shared with other devices or shared with a fertility doctor using a desktop or mobile application and the Internet. Architecture 200 also includes I/O port 212 (e.g., a USB port) and I/O controller 205 for wired communication with other devices and for powering charging dock 103. To protect the user's privacy, in an embodiment a handheld radio frequency identifier (RFID) reader can be used by the doctor to read private user data from FAS 100 through a local area network (e.g., through the user' WiFi network).

Audio subsystem 214 can be used to generate spoken questions through loudspeaker 215 using a text to speech converter, and also receive spoken responses to the questions from the user through microphone(s) 216. Audio subsystem 214 can include a speech recognition engine for converting the speech into text so that it can be used to generate fertility awareness data. In an embodiment, audio subsystem 215 can include a media player for playing music or audio effects. This allows the charging dock 103 to perform other useful tasks, such as a smart speaker or digital alarm clock. Internet connectivity through RF TX 202 can allow the user to access other online services, such as news feeds, Internet radio, searching, shopping, ordering food, making telephone calls, etc.

FA device 102 can be charged by charging dock 103 when docked using electrode(s)/contact(s) 213a. A power cord 213b can be used to power charging dock 103 from a wall outlet. In an embodiment, photovoltaic cell(s) 209 and/or induction coil(s), together with charge circuit 208 can be used to charge FA device 102. Inductions coil(s) can also be used with RF TX in RFID reader application described above.

Figure 3:
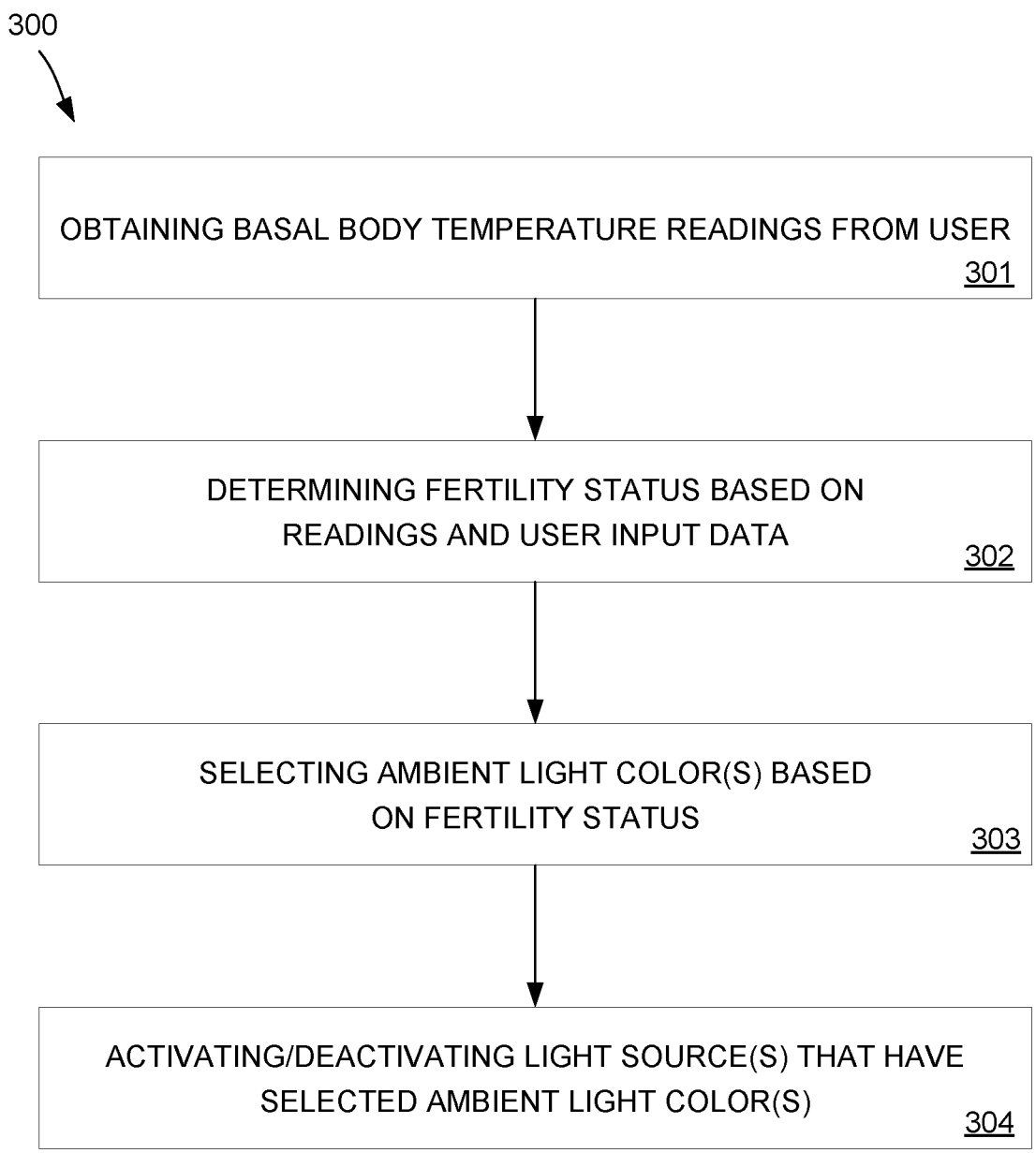
FIG. 3 is a flow diagram of a process for determining a fertility window, according to an embodiment.

FIG. 3 is a flow diagram of process 300 for determining a fertility window, according to an embodiment. Process 300 can be implemented using the architecture described in reference to FIG. 2.

Process 300 can begin by obtaining, by a biosensor, basal body temperature readings of a user (301). Process 300 continues by determining, by a processor, a fertility status of the user based on the basal body temperature readings and user input data (302). For example, the user input data can be obtained by the device in response to a series of questions asked by the device through a digital assistant, such as the user's age, length of the user's cycle, the user's known fertility problems, etc. The user's answers can be received by one or more microphones converted into text, which can be used together with the temperature readings to create a map of the user's menstrual cycle. Process 300 continues by selecting, by the one or more processors and based on the determined fertility status, one or more ambient light colors (303). Process 300 continues by activating, an ambient light indicator system, one or more ambient light sources having the selected one or more ambient light colors (304).

The features described may be implemented in digital electronic circuitry or in computer hardware, firmware, software, or in combinations of them. The features may be implemented in a computer program product tangibly embodied in an information carrier, e.g., in a machine-readable storage device, for execution by a programmable processor. Method steps may be performed by a programmable processor executing a program of instructions to perform functions of the described implementations by operating on input data and generating output.

The described features may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., Objective-C, Java), including compiled or interpreted languages, and it may be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random-access memory or both. The processor and the memory may be supplemented by, or incorporated in, ASICs (application-specific integrated circuits).

Storage devices suitable for tangibly embodying computer program instructions and data include all forms of non-volatile memory, including by way of example, semiconductor memory devices, such as EPROM, EEPROM, and flash memory devices.

To provide for interaction with a user the features may be implemented on a computer having a display device such as a LED (light emitting diode), LCD (liquid crystal display) display, OLED or touch display.

A number of implementations have been described. Nevertheless, it will be understood that various modifications may be made. Elements of one or more implementations may be combined, deleted, modified, or supplemented to form further implementations. In yet another example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. An apparatus comprising:
a disc-shaped housing having a top surface and a bottom surface, the bottom surface configured to fit into a disc-shaped recess of a charging dock;
an ambient light indicator system disposed within the housing and including one or more ambient light sources for projecting ambient light through the top surface of the housing while the apparatus is docked in the charging dock;
a temperature sensor disposed on the bottom surface, the temperature sensor configured to capture a basal body temperature reading from a forehead of a user;
a charge circuit and one or more charge electrodes or contacts configured to charge the apparatus when the apparatus is docked in the recess of the charging dock;
an output port configured to transfer data to the charging dock when the apparatus is docked;
a printed circuit board disposed within the housing and including:
one or more processors coupled to the temperature sensor;
memory storing computer-readable instructions that when executed by the one or more processors, cause the one or more processors to perform operations comprising:
obtaining, by the one or more processors, the user's basal body temperature reading from the temperature sensor;
storing, by the one or more processors, the user's basal body temperature reading in the memory;
determining, by the one or more processors, that the apparatus is docked in the docking station; and
transferring, by the one or more processors, the basal body temperature reading from the memory to the output port.

2. The apparatus of claim 1, wherein at least a portion of the top or bottom surface is touch sensitive.

3. A system comprising:
a disc-shaped fertility awareness (FA) apparatus including:
a disc-shaped housing having a top surface and a bottom surface, the bottom surface configured to fit into a disc-shaped recess of a charging dock;
an ambient light indicator system disposed within the housing and including one or more ambient light sources for projecting ambient light through the top surface of the housing while the apparatus is docked in the charging dock;
a temperature sensor disposed on the bottom surface, the temperature sensor configured to capture a basal body temperature reading from a forehead of a user;
a charge circuit and one or more charge electrodes or contacts configured to charge the apparatus when the apparatus is docked in the recess of the charging dock;
an output port configured to transfer data to the charging dock when the apparatus is docked;
a printed circuit board disposed within the housing and including:
one or more processors coupled to the temperature sensor;
memory storing computer-readable instructions that when executed by the one or more processors, cause the one or more processors to perform operations comprising:
obtaining, by the one or more processors, the user's basal body temperature reading from the temperature sensor;
storing, by the one or more processors, the user's basal body temperature reading in the memory;
determining, by the one or more processors, that the apparatus is docked in the docking station; and
transferring, by the one or more processors, the basal body temperature reading from the memory to the output port; and
a charging dock for the FA apparatus including:
a housing having a top surface and a bottom surface, the top surface having a disc-shaped recess for receiving the FA apparatus;
an ambient light indicator system disposed within the housing and including one or more ambient light sources for projecting ambient light through the top surface of the housing while the apparatus is docked in a charging dock;

a printed circuit board disposed within the housing and including:

one or more processors coupled to the ambient light indicator system;

memory storing computer-readable instructions that when executed by the one or more processors, cause the one or more processors to perform operations comprising:

obtaining, by the one or more processors, one or more basal body temperature readings from an output port of the FA apparatus and user input data from memory;

determining, by the one or more processors, fertility awareness information from the basal body temperature readings and the user input data;

responsive to the determining, commanding, by the one or more processors, the ambient light indicator system to activate or deactivate one or more ambient light sources in accordance with the fertility awareness information to indicate a fertility status.

4. The apparatus of claim 3, further comprising:
one or more audio loudspeakers;
one or more microphones; and
an audio subsystem coupled to the one or more processors, the one or more microphones and the one or more audio loudspeakers.

5. The apparatus of claim 3, wherein the apparatus further comprises:
a rechargeable battery for supplying power to at least the one or more processors;
a charging circuit coupled to the rechargeable battery; and
one or more photovoltaic cells coupled to the charging circuit.

6. The apparatus of claim 5, wherein the apparatus further comprise one or more inductive coils and the charging circuit is configured for inductive charging.

7. The apparatus of claim 3, wherein the memory includes instructions to instantiate a digital assistant on the apparatus for receiving voice commands and/or responding to spoken requests or questions.

8. The apparatus of claim 3, further comprising:
a touch-sensitive display configured to receive touch input.

9. The apparatus of claim 3, further comprising:
a wireless transceiver configured to transmit data to another device and to receive over-the-air (OTA) programming; and
one or more physical ports for wired connection to one or more devices.

10. The apparatus of claim 3, wherein the user input data is encrypted.

11. The apparatus of claim 3, wherein determining, by the one or more processors, the fertility awareness information further comprises:
applying a machine learning algorithm to at least one of a history of basal temperature readings or a history of user input data.

12. The apparatus of claim 3, wherein the fertility awareness information indicates at least one of a time of maximum fertility or a time of minimum fertility.

13. A method comprising:
obtaining, by a charging dock, basal body temperature readings captured from a forehead of a user from a disc-shaped fertility awareness (FA) apparatus placed in a disc-shaped recess of the charging dock;
determining, by one or more processors of a charging dock, a fertility status of the user based on the basal body temperature readings and user input data;
selecting, by the one or more processors and based on the determined fertility status, one or more ambient light colors; and
activating, one or more ambient light sources having the selected one or more ambient light colors, wherein the ambient light colors are projected through a top surface of a housing of the FA apparatus while the FA apparatus is docked in the charging dock.

14. The method of claim 13, wherein determining, by the one or more processors, the fertility status of the user further comprises:
applying a machine learning algorithm to at least one of a history of basal temperature readings or a history of user input data.

15. The method of claim 13, wherein the fertility status of the user indicates at least one of a time of maximum fertility or a time of minimum fertility.

16. The method of claim 13, further comprising:
outputting, by the processor, a question based on the fertility status;
receiving, by the processor, a response to the question;
updating, by the processor, the fertility status; and
storing, by the processor, the updated fertility status.

17. The method of claim 13, further comprising:
detecting the presence of a radio frequency identifier (RFID) reader;
responsive to the detecting, outputting the fertility status to the RFID reader.

* * * * *